United States Patent
Levy et al.

(10) Patent No.: US 8,133,232 B2
(45) Date of Patent: Mar. 13, 2012

(54) EXPANDABLE BONE DEVICE

(75) Inventors: Mark M. Levy, Raanana (IL); Eyal Zylberberg, Kfar Yona (IL); Yair Spanier, Pardes Hanna (IL); Amnon Yadin, Kfar Vitkin (IL); Raphael Meloul, Jerusalem (IL)

(73) Assignee: Expanding Orthopedics Inc., Memphis, TN (US)

( * ) Notice: Subject to any disclaimer, the term of this patent is extended or adjusted under 35 U.S.C. 154(b) by 682 days.

(21) Appl. No.: 11/778,675

(22) Filed: Jul. 17, 2007

(65) Prior Publication Data
US 2009/0024217 A1    Jan. 22, 2009

(51) Int. Cl.
*A61B 17/58* (2006.01)
*A61B 17/60* (2006.01)
*A61F 2/00* (2006.01)

(52) U.S. Cl. .............. 606/90; 623/17.11; 623/17.16

(58) Field of Classification Search .... 623/17.11–17.16; 606/90
See application file for complete search history.

(56) References Cited

U.S. PATENT DOCUMENTS

| | | | |
|---|---|---|---|
| 6,126,689 A | 10/2000 | Brett | |
| 2002/0128716 A1 | 9/2002 | Cohen | |
| 2003/0171813 A1 | 9/2003 | Kiester | |
| 2008/0114367 A1 * | 5/2008 | Meyer | 606/90 |

FOREIGN PATENT DOCUMENTS

WO   01/66047   9/2001

* cited by examiner

*Primary Examiner* — Eduardo C Robert
*Assistant Examiner* — Christina Negrelli
(74) *Attorney, Agent, or Firm* — Dekel Patent Ltd.; David Klein

(57) ABSTRACT

An expandable bone device including first and second bone support elements, a manipulator positioned between the first and second bone support elements and connected to them by link members, the manipulator adapted to move the first and second bone support elements between a collapsed orientation and an expanded orientation, wherein in the collapsed orientation the first and second bone support elements are drawn towards the manipulator and in the expanded orientation the first and second bone support elements are moved outwards away from a longitudinal axis of the manipulator, and deformable support struts connected between the manipulator and the first and second bone support elements that deform when moved by the manipulator from the collapsed orientation to the expanded orientation and vice versa, wherein in the expanded orientation the deformable support struts form a structure that maintains the first and second bone support elements in the expanded orientation.

11 Claims, 4 Drawing Sheets

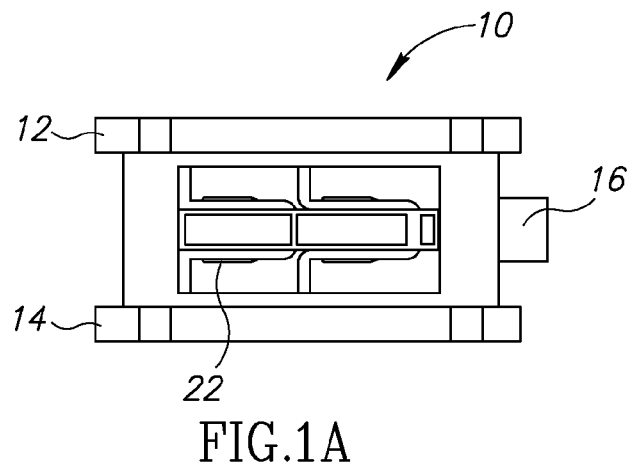
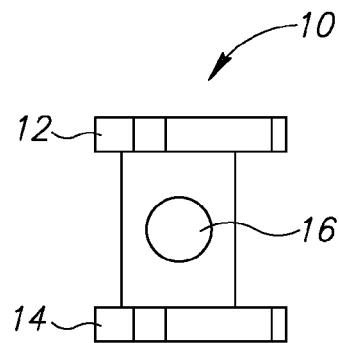
FIG.1A  FIG.1B
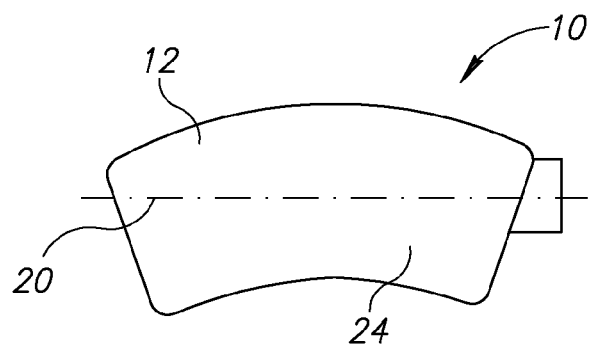
FIG.1C
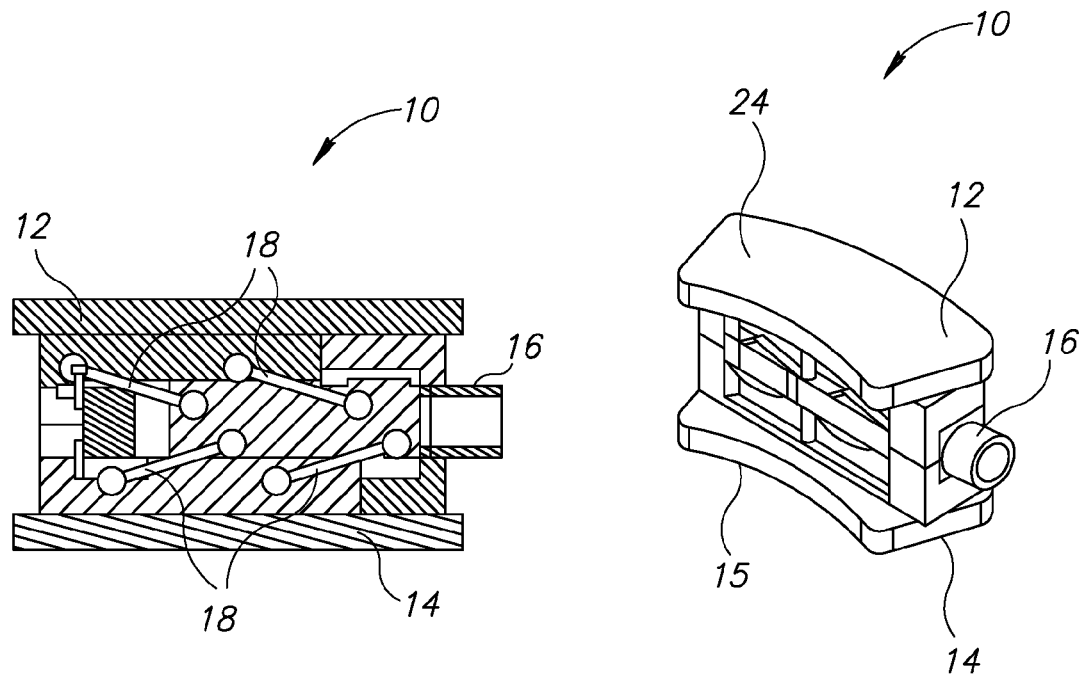
FIG.1D  FIG.1E

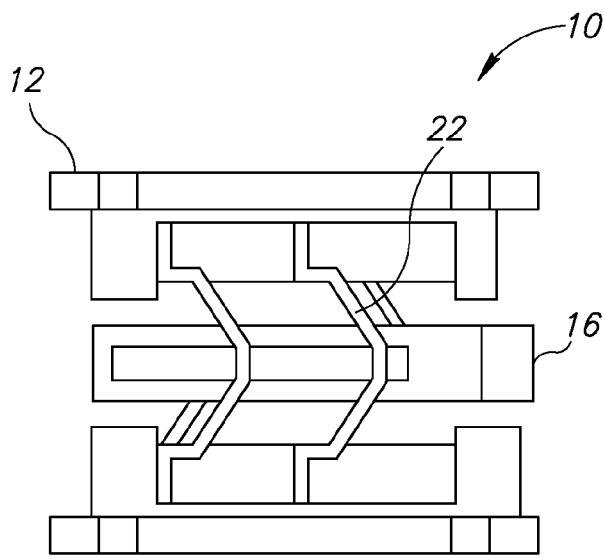
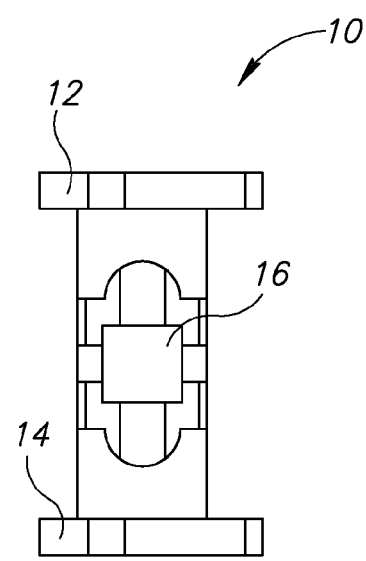
FIG.2A  FIG.2B
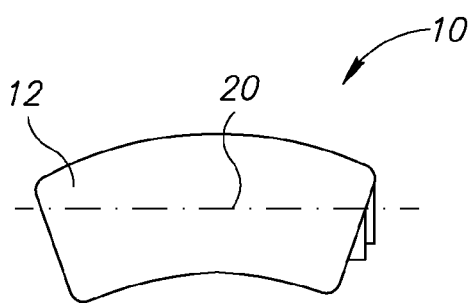
FIG.2C
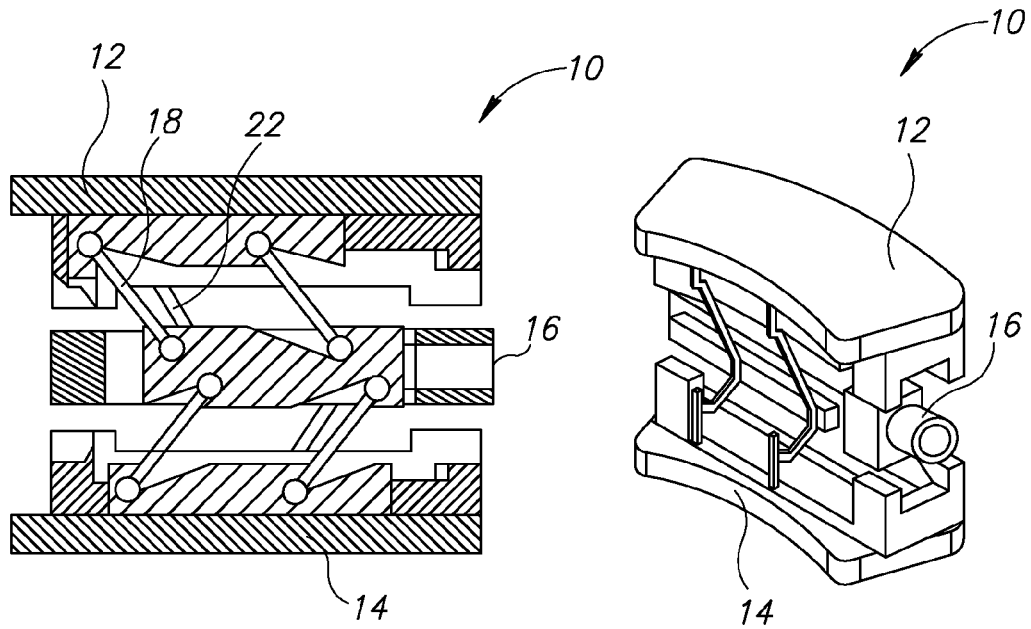
FIG.2D  FIG.2E

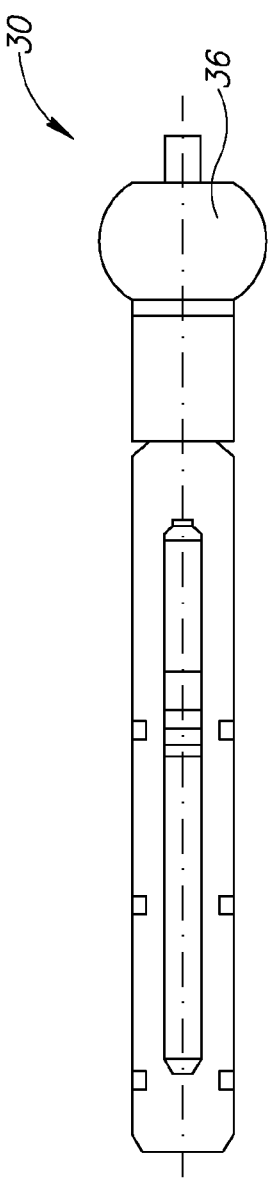
FIG.3A
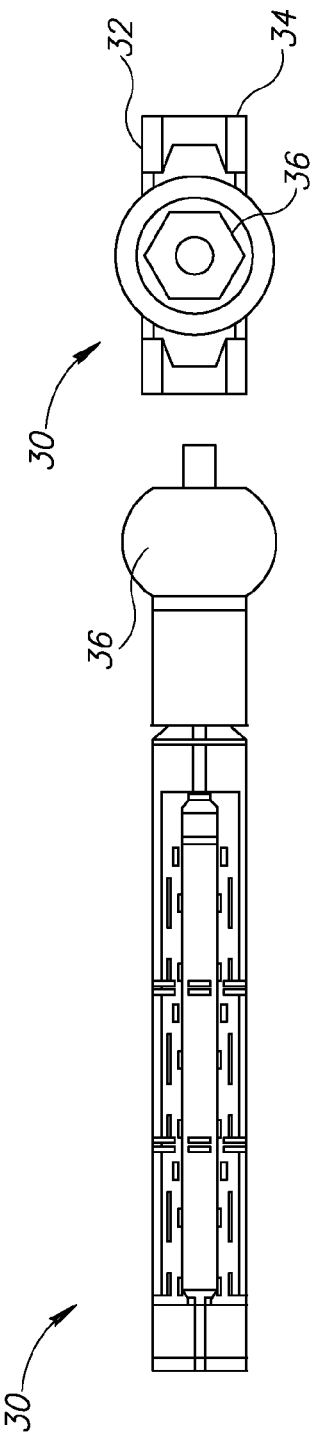
FIG.3B
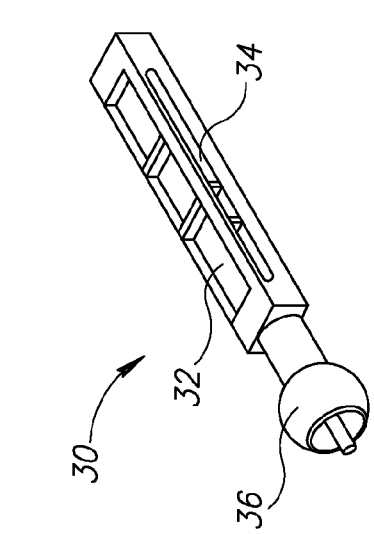
FIG.3C
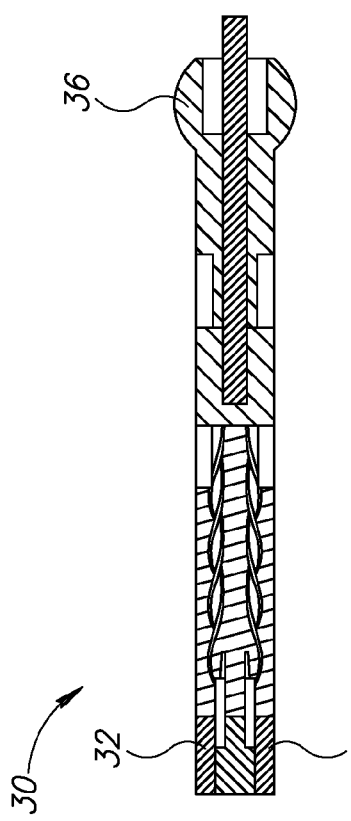
FIG.3E
FIG.3D

EXPANDABLE BONE DEVICE

FIELD OF THE INVENTION

The present invention relates generally to expandable bone devices, such as but not limited to, devices for vertebral body reconstruction (vertebroplasty), such as for treatment of compression fractures (e.g., the thoracic and lumbar spine area), or for an expandable bone device for transversely or axially displacing structures (e.g., in the spine).

BACKGROUND OF THE INVENTION

Various instruments and methods for the treatment of compression-type bone fractures and other osteoporotic and/or non-osteoporotic conditions have been developed. In one method, a cavity may be formed in the bone to be treated, followed by the insertion of an inflatable balloon-like device into the bone cavity. Inflation of the balloon-like device causes a compaction of the cancellous bone and/or bone marrow against the inner cortical wall of the bone, thereby resulting in enlargement of the bone cavity and/or reduction of the compression fracture. The balloon-like device is then deflated and removed from the bone cavity. A biocompatible filling material, such as methylmethacrylate cement or a synthetic bone substitute, is sometimes delivered into the bone cavity and allowed to set to a hardened condition to provide internal structural support to the bone.

However, it has been found that expansion of the balloon-like device is not readily controllable. Instead, when such balloon-like device is inflated, expansion occurs along a path of least resistance. As a result, the direction of compaction of the cancellous bone and/or reduction of the compression fracture is not controllable, and expansion occurs in multiple directions and along multiple axes. In addition, the expansion of the balloon-like device does not remain at its original expansive state and changes over time. The cement may also cause new fractures in adjacent levels.

U.S. Pat. No. 6,554,833 to Levy et al. describes a device for stabilizing bone, which includes a tubular body having first and second end regions defining a longitudinal axis therebetween. A plurality of splines extend from the first end region, the splines including first ends coupled to the first end region, and second ends disposed away from the first end region, the second ends being directable from a generally axial collapsed state to a substantially transverse expanded state. A plurality of support arms are coupled to the splines, and an actuator is coupled to the support arms, the actuator movable axially relative to the elongate body for causing the support arms to direct the second ends of the splines from the collapsed state to the expanded state. Optionally, the device includes another set of splines extending from the second end region or located at an intermediate region of the tubular body.

SUMMARY OF THE INVENTION

The present invention seeks to provide an expandable bone device, as is described in detail further hereinbelow. The expandable bone device of the invention may be described hereinbelow for use with the spine (e.g., the pedicles, transverse or spine processes, disc spaces and the like), but it is emphasized that the invention is not limited to the spine, and may be used for any bone, such as but not limited to, calcareous, distal radius, upper tibia, hand bones and bone epiphysis. The invention may be used in the treatment of any bone disease, disorder or problem, such as but not limited to, fractures, prevention of trauma or fractures due to osteoporosis, endocrine, metabolic or tumoral bone diseases, AVN and trauma and disc diseases, with minimally invasive techniques or open surgery. The invention may be used as "scaffolding" to support or manipulate bone structures, such as for filling bone structures (e.g., with cement, bone graft, bone substitutes or collagen and other materials), or for correction of deformities during instrumentation, and may or may not be left in the bone structure, depending on the procedure used.

There is thus provided in accordance with an embodiment of the present invention an expandable bone device including first and second bone support elements, a manipulator positioned between the first and second bone support elements and connected to them by link members, the manipulator adapted to move the first and second bone support elements between a collapsed orientation and an expanded orientation, wherein in the collapsed orientation the first and second bone support elements are drawn towards the manipulator and in the expanded orientation the first and second bone support elements are moved outwards away from a longitudinal axis of the manipulator, and deformable support struts connected between the manipulator and the first and second bone support elements that deform when moved by the manipulator from the collapsed orientation to the expanded orientation and vice versa, wherein in the expanded orientation the deformable support struts form a structure (which may or may not be rigid) that maintains the first and second bone support elements in the expanded orientation.

The expandable bone device may include one or more of the following non-limiting features. For example, in the expanded orientation, the deformable support struts oppose forces directed normal to bone support faces of the first and second bone support elements so as to maintain the first and second bone support elements in the expanded orientation. The deformable support struts pass through a phase of elastic instability when moved by the manipulator from the collapsed orientation to the expanded orientation and vice versa. The link members maintain parallelism between the first and second bone support elements throughout movement between the collapsed and expanded orientations.

The link members may be hinged to the first and second bone support elements. The manipulator may move the first and second bone support elements between the collapsed and expanded orientations by moving linearly along its longitudinal axis or by screw turning about its longitudinal axis. Bone support faces of the first and second bone support elements may be flat and rectangular (or not rectangular).

BRIEF DESCRIPTION OF THE DRAWINGS

The present invention will be understood and appreciated more fully from the following detailed description taken in conjunction with the drawings in which:

FIGS. 1A, 1B, 1C, 1D and 1E are simplified side-view, end-view, top-view, sectional side-view and perspective illustrations, respectively, of an expandable bone device, constructed and operative in accordance with an embodiment of the present invention, in a collapsed orientation;

FIGS. 2A, 2B, 2C, 2D and 2E are simplified side-view, end-view, top-view, sectional side-view and perspective illustrations, respectively, of the expandable bone device of FIGS. 1A-1E in an expanded orientation;

FIGS. 3A, 3B, 3C, 3D and 3E are simplified side-view, top-view, end-view, sectional side-view and perspective illustrations, respectively, of an expandable bone device, constructed and operative in accordance with another embodiment of the present invention, in a collapsed orientation.

DETAILED DESCRIPTION OF EMBODIMENTS

Figure 4A:
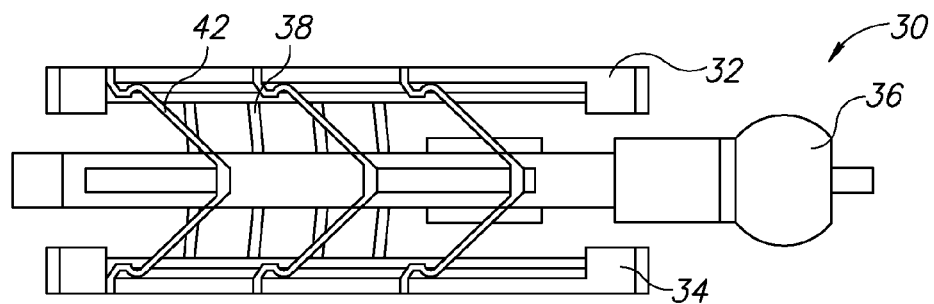
FIGS. 4A, 4B, 4C, 4D and 4E are simplified side-view, top-view, end-view, sectional side-view and perspective illustrations, respectively, of the expandable bone device of FIGS. 3A-3E in an expanded orientation.

Reference is now made to FIGS. 1A-1E and FIGS. 2A-2E, which illustrate an expandable bone device 10, constructed and operative in accordance with a non-limiting embodiment of the present invention.

In the illustrated embodiment, expandable bone device 10 includes first and second bone support elements 12 and 14. A manipulator 16 is positioned between first and second bone support elements 12 and 14 and connected to them by link members 18.

The expandable bone device 10 may be constructed, without limitation, of medically safe metals (e.g., stainless steel, titanium or titanium alloys, cobalt-chromium or other alloys, shape memory alloys, such as NITINOL), plastics, including PEEK, resorbable materials and shape memory polymers, or bone, such as allograft or bone derivatives, or any combination of the above.

One or more of first and second bone support elements 12 and 14 may be non-smooth for enhancing adhesion to bone structure. Additionally or alternatively, one or more of first and second bone support elements 12 and 14 may be coated with a material that enhances adhesion with bone, such as but not limited to, hydroxyapatite, or other biological materials, such as but not limited to, bone factors, biphosphonates, antibiotics, or antineoplastic drugs. The support elements 12 and 14 in the illustrated embodiment of FIGS. 1A-2E have bone support faces 24 which are flat and non-rectangular—they are shown arcuate but may be any other shape and size as well.

Manipulator 16 can move first and second bone support elements 12 and 14 between a collapsed orientation (FIGS. 1A-1E) and an expanded orientation (FIGS. 2A-2E), as is described more in detail hereinbelow. In the collapsed orientation, first and second bone support elements 12 and 14 are drawn towards manipulator 16. In the expanded orientation, first and second bone support elements 12 and 14 are moved outwards away from a longitudinal axis 20 of manipulator 16.

Without limitation, manipulator 16 may be similar to the actuator (also referred to as the elongate control member) shown and described with reference to the embodiment of FIGS. 12-15D in U.S. Pat. No. 6,554,833, the disclosure of which is incorporated herein by reference. In the illustrated embodiment, manipulator 16 includes a rod (for example, made of stainless steel or titanium alloy or any other suitable material) to which link members 18 are hinged. Pushing rod along longitudinal axis 20 to the left in the sense of FIG. 1D causes link members 18 to pivot about the hinged connections and expand outwards to the position shown in FIG. 2D. This is the expanded orientation in which first and second bone support elements 12 and 14 are separated from one another and generally parallel to each other at all times in their travel. Manipulator 16 can have some attachments or notches for an inserting tool that can be operated in different orientations, depending upon the particular application.

Deformable support struts 22 (seen best in FIGS. 2A and 2D, but also seen in FIG. 1A) are connected between manipulator 16 and first and second bone support elements 12 and 14. Deformable support struts 22 may be constructed, without limitation, of medically safe, resilient materials (e.g., stainless steel, titanium, cobalt-chromium, shape memory alloys, such as NITINOL or other alloys or polymers). Deformable support struts 22 deform when moved by manipulator 16 from the collapsed orientation to the expanded orientation and vice versa. In the expanded orientation, deformable support struts 22 form a rigid structure that maintains first and second bone support elements 12 and 14 in the expanded orientation. More specifically, in the expanded orientation, the deformable support struts 22 may oppose forces directed normal to bone support faces 24 of first and second bone support elements 12 and 14 so as to maintain first and second bone support elements 12 and 14 in the expanded orientation. Deformable support struts 22 pass through a phase of elastic instability (they buckle) when moved by manipulator 16 from the collapsed orientation to the expanded orientation and vice versa. Link members 18 maintain parallelism between first and second bone support elements 12 and 14 throughout movement between the collapsed and expanded orientations.

Figure 4B:
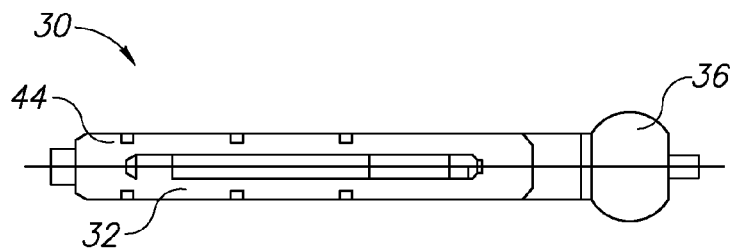
Figure 4C:
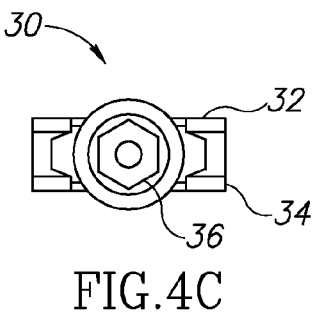
Figure 4D:
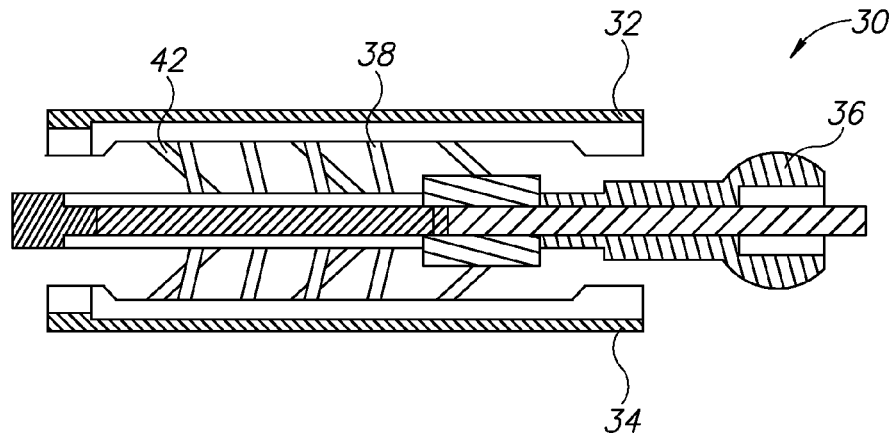
Figure 4E:
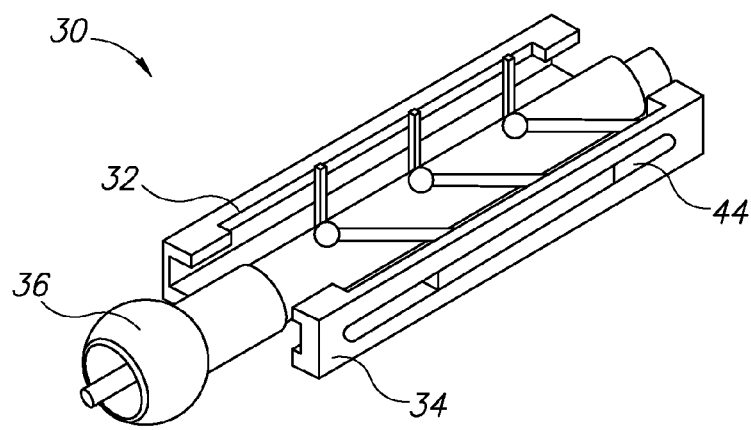

Reference is now made to FIGS. 3A-3E and FIGS. 4A-4E, which illustrate an expandable bone device 30, constructed and operative in accordance with a non-limiting embodiment of the present invention.

In the illustrated embodiment, expandable bone device 30 includes first and second bone support elements 32 and 34. A manipulator 36 is positioned between first and second bone support elements 32 and 34 and connected to them by link members 38.

As above, first and second bone support elements 32 and 34 may be non-smooth for enhancing adhesion to bone structure, and/or coated with a material that enhances adhesion with bone. The support elements 32 and 34 in the illustrated embodiment of FIGS. 3A-4E have bone support faces 44 which are flat and rectangular, but may be any other shape and size as well.

Manipulator 36 can move first and second bone support elements 32 and 34 between a collapsed orientation (FIGS. 3A-3E) and an expanded orientation (FIGS. 4A-4E), as is described more in detail hereinbelow. In the collapsed orientation, first and second bone support elements 32 and 34 are drawn towards manipulator 36. In the expanded orientation, first and second bone support elements 32 and 34 are moved outwards away from a longitudinal axis 40 of manipulator 36. Manipulator 36 can have some attachments or notches for an inserting tool that can be operated in different orientations, depending upon the particular application. In addition, manipulator 36 can have a section with external threads that may allow it to be screwed into a bone structure adjacent to the one to be expanded, e.g., a bone cortex or a pedicle canal.

Without limitation, manipulator 36 may be a threaded rod with a screwdriver head (e.g., hexagonal Allen head or screwdriver slot) and link members 38 are hinged to this rod. Turning (screwing) rod about longitudinal axis 40 causes link members 38 to pivot about the hinged connections and expand outwards to the position shown in FIG. 4D. This is the expanded orientation in which first and second bone support elements 32 and 34 are separated from one another and generally parallel to each other at all times in their travel.

Deformable support struts 42 (seen best in FIGS. 4A and 4D, but also seen in FIG. 3B) are connected between manipulator 36 and first and second bone support elements 32 and 34 Deformable support struts 42 deform when moved by manipulator 36 from the collapsed orientation to the expanded orientation and vice versa. In the expanded orientation, deformable support struts 42 form a rigid structure that maintains first and second bone support elements 32 and 34 in the expanded orientation. More specifically, in the expanded orientation, the deformable support struts 42 may oppose forces directed normal to bone support faces 44 of first and second bone support elements 32 and 34 so as to maintain first and second bone support elements 32 and 34 in the expanded orientation. Deformable support struts 42 pass through a phase of elastic instability (they buckle) when moved by manipulator 36 from the collapsed orientation to the expanded orientation and vice versa. Link members 38 maintain parallelism between first and second bone support elements 32 and 34 throughout movement between the collapsed and expanded orientations. In this embodiment, a connector may be used to link the device with another device (same as the first device or a different device), to anchor the device (or the combination of the device and another device) in the same vertebra or adjacent vertebra or at distant levels.

It is noted that first and second bone support elements 32 and 34 (and also 12 and 14) may be of any shape and size, depending on the medical application. For example, instead of being flat, the bone support faces 44 of first and second bone support elements 32 and 34 may be U-shaped or rounded to hold a process or other anatomical structure. In addition, a plurality of openings can be formed in the first and or the second bone support elements 12, 14, 32 and 34. Manipulator 36 may be locked in place to increase the stability in the expanded position.

Furthermore, some spine curvature correction can be achieved with the device by adding some curvature to the bone support elements, or to a section of them, when using one or two per level. On the other hand, some curvature can also be achieved by asymmetrical lengths of link members, or a combination of curvature of the bone support elements and asymmetric link members, such that when deployed, the devices can make some degree of correction of kyphosis, lordosis, scoliosis or combinations of them.

It is appreciated that various features of the invention which are, for clarity, described in the contexts of separate embodiments, may also be provided in combination in a single embodiment. Conversely, various features of the invention which are, for brevity, described in the context of a single embodiment, may also be provided separately or in any suitable subcombination.

What is claimed is:

1. An expandable bone device comprising:
   first and second bone support elements;
   a manipulator positioned between said first and second bone support elements and connected to them by link members, said manipulator adapted to move said first and second bone support elements between a collapsed orientation and an expanded orientation, wherein in the collapsed orientation said first and second bone support elements are drawn towards said manipulator and in the expanded orientation said first and second bone support elements are moved outwards away from a longitudinal axis of said manipulator; and
   deformable support struts connected between said manipulator and said first and second bone support elements that deform when moved by said manipulator from the collapsed orientation to the expanded orientation and vice versa, wherein in the expanded orientation said deformable support struts form a structure that maintains said first and second bone support elements in the expanded orientation, and wherein said deformable support struts pass through a phase of elastic instability when moved by said manipulator from the collapsed orientation to the expanded orientation and vice versa.

2. The expandable bone device according to claim 1, wherein in the expanded orientation said deformable support struts oppose forces directed normal to bone support faces of said first and second bone support elements so as to maintain said first and second bone support elements in the expanded orientation.

3. The expandable bone device according to claim 1, wherein said link members maintain parallelism between said first and second bone support elements throughout movement between the collapsed and expanded orientations.

4. The expandable bone device according to claim 1, wherein said link members are hinged to said first and second bone support elements.

5. The expandable bone device according to claim 1, wherein said manipulator moves said first and second bone support elements between the collapsed and expanded orientations by moving linearly along its longitudinal axis.

6. The expandable bone device according to claim 1, wherein said manipulator moves said first and second bone support elements between the collapsed and expanded orientations by screw turning about its longitudinal axis.

7. The expandable bone device according to claim 1, wherein bone support faces of said first and second bone support elements are flat and rectangular.

8. The expandable bone device according to claim 1, wherein bone support faces of said first and second bone support elements are flat and not rectangular.

9. The expandable bone device according to claim 1, wherein bone support faces of said first and second bone support elements are not flat.

10. The expandable bone device according to claim 1, wherein said manipulator is locked in the expanded position.

11. An expandable bone device comprising:
    first and second bone support elements;
    a manipulator positioned between said first and second bone support elements and connected to them by link members, said manipulator adapted to move said first and second bone support elements between a collapsed orientation and an expanded orientation, wherein in the collapsed orientation said first and second bone support elements are drawn towards said manipulator and in the expanded orientation said first and second bone support elements are moved outwards away from a longitudinal axis of said manipulator; and
    deformable support struts connected between said manipulator and said first and second bone support elements that deform when moved by said manipulator from the collapsed orientation to the expanded orientation and vice versa, wherein in the expanded orientation said deformable support struts oppose forces directed normal to bone support faces of said first and second bone support elements so as to maintain said first and second bone support elements in the expanded orientation, and wherein said deformable support struts pass through a phase of elastic instability when moved by said manipulator from the collapsed orientation to the expanded orientation and vice versa, and wherein said link members maintain parallelism between said first and second bone support elements throughout movement between the collapsed and expanded orientations, and wherein said deformable support struts pass through a phase of elastic instability when moved by said manipulator from the collapsed orientation to the expanded orientation and vice versa.

* * * * *